United States Patent [19]
Bell et al.

[11] Patent Number: 5,800,372
[45] Date of Patent: Sep. 1, 1998

[54] FIELD DRESSING FOR CONTROL OF EXSANGUINATION

[75] Inventors: Eugene Bell, 305 Commonwealth Ave., Boston, Mass. 02115; Aslam A. Malik, Cameron Park, Calif.; Boris Nahlovsky, Cameron Park, Calif.; Marvin F. Young, El Dorado Hills, Calif.

[73] Assignees: Aerojet-General Corporation, Rancho Cordova, Calif.; Eugene Bell, Boston, Mass.

[21] Appl. No.: 584,041

[22] Filed: Jan. 9, 1996

[51] Int. Cl.⁶ .................................................. A61F 13/00
[52] U.S. Cl. ..................... 602/48; 128/DIG. 8; 602/49; 424/447; 424/484

[58] Field of Search .................... 424/443, 445, 424/484, 448, 447, 532, 487, 491, 494, 492; 602/48, 49; 604/304, 307; 128/DIG. 8

[56] References Cited

U.S. PATENT DOCUMENTS 5,056,510  10/1991  Gilman ...................................... 602/52

Primary Examiner—Robert A. Clarke
Attorney, Agent, or Firm—Townsend and Townsend and Crew LLP

[57] ABSTRACT

Microfibrillar collagen and a superabsorbent polymer are combined in a hemostatic bandage which both absorbs blood and induces clotting.

24 Claims, 2 Drawing Sheets

5,800,372

FIELD DRESSING FOR CONTROL OF EXSANGUINATION

BACKGROUND OF THE INVENTION

One of the major causes of death among troops killed in action other than those who are killed instantly is exsanguination. The control of topical bleeding is thus of critical importance in the armed forces and is likewise of importance for civilian use such as trauma treatment and the general administration of first aid.

Cotton gauze pads capable of absorbing 250 mL of blood are the principal dressings currently in use by the armed forces and by civilian trauma units for external hemorrhage. These pads are passive dressings, however, unable to initiate or accelerate blood clotting. An alternate solution recently proposed is a hemostatic pressure bandage containing fibrin glue formed by combining bovine fibrinogen and thrombin, as reported by Larson, M. J., et al., *Arch. Surg.* 130:420–422 (1995), who tested it to control injured arteries in a swine model. Although blood loss was reduced by a factor of 6 in the first hour of application, fibrin glue has the disadvantage of carrying the risk of transmitting serological disease from the blood serving as the sources of the two components. Further disadvantages are that, to form an effective glue, the components must be kept separate from each other until the time of use, and that thrombin must be maintained at a temperature of 30° C. or below.

SUMMARY OF THE INVENTION

It has now been discovered that a hemostatic wound dressing containing a mixture of superabsorbent polymer and microfibrillar collagen provides rapid intervention of exsanguination more effectively than cotton gauze. As a mixture of particles, the combination of these two materials efficiently initiates clotting and arrests hemorrhaging, while promoting rapid clot propagation in a direction opposing that of the blood flow. The particle mixture is retained in a pouch, envelope or enclosure in general of flexible and blood-permeable material, forming the major structural component of the bandage. The enclosure is preferably expandable to accommodate the expansion of the superabsorbent polymer as the polymer absorbs fluid from the blood escaping from the wound. Preferred embodiments of the invention also include baffles, partitions or other stabilizing structures to reduce or eliminate the shifting of the particles within the enclosure. Baffles and partitions when included can be expandable themselves to further accommodate the expansion of the superabsorbent polymer. Additional layers of material affixed to the exterior of the enclosure can also be included to serve, for example, as a skin-contacting and protecting layer on one side while permitting the blood to pass through and a exterior protective layer on the other side. Finally, the dressing can also contain securing members such as straps, loops, fastening strips, or adhesive-backed regions to secure the dressing to the wound surface.

Further features and advantages of the invention will become apparent from the description that follows.

DETAILED DESCRIPTION OF THE INVENTION AND PREFERRED EMBODIMENTS

Figure 2:
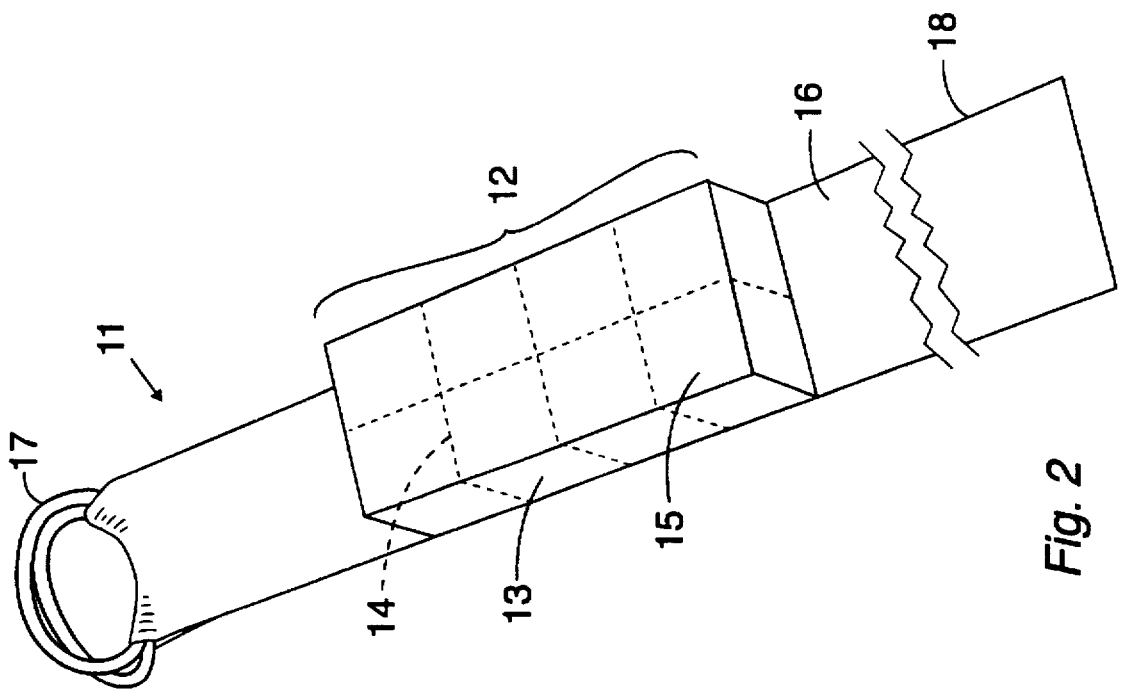
FIG. 2 is the same perspective view as FIG. 1, differing only in that the active region of the dressing has been expanded by absorption of blood.

Microfibrillar collagen is a solid derived from collagen, a polypeptide naturally occurring in animal sources. While a variety of animal sources can be used, bovine and porcine collagen are the most commonly used starting materials for microfibrillar, and skin and bone tissue are preferred as the tissues from which the collagen is extracted.

Methods of extracting collagen and treating it to convert it to the microfibrillar form are known in the biotechnology industry. One such method which uses animal skin as the source begins with the depilation and defatting of the tissue, then thawing the tissue and washing it first in bleach and then in sterile water. The tissue is then soaked in a mixture of 10% ammonium chloride and 5% calcium hydroxide for two hours, depilated further and washed in buffered water. This is followed by grinding of the tissue to particles 0.5 to 5 mm in diameter, which are then soaked first in sterile water for 24 hours and then in 70% ethanol for 16 hours. The particles are then either oven dried or lyophilized, then milled and sieved to the desired size.

An example of a method which uses bone as the source of collagen is as follows. After tendons have been removed by mechanical means, the bone tissue is cleaned with bleach, washed in sterile water, oven dried, and then washed first in 70% ethanol and then in sterile water. The tissue is then coarse-ground and washed and oven-dried again, then milled and sieved to the desired size range. The resulting particles are soaked in 0.5N aqueous HCl for three hours to remove all mineral content, then washed and dried.

The microfibrillar collagen can assume any physical form which can be contained or built into a topical wound dressing. Common forms of microfibrillar collagen are powders and webs. Powders are preferred in view of their high surface area and the ease by which they can be mixed with superabsorbent polymer. For powders, the particle size can vary widely and is not critical to this invention. In most applications, however, best results will be obtained with particles which are substantially entirely within the size range of about 1 micron to about 1000 microns in diameter. A preferred size range is about 20 microns to about 500 microns in diameter, while a particularly preferred size range is about 100 microns to about 200 microns in diameter.

Microfibrillar collagen is commercially available, sold under the product name AVITENE by Alcon Laboratories, Inc., of Fort Worth, Tex., USA, MedChem Products, Inc., of Woburn, Mass., USA, and Tissue Engineering Co., of Boston, Mass., USA. Microfibrillar collagen is currently used to arrest bleeding, particularly during surgery.

Superabsorbent polymers are well known in the art of polymer technology for use in absorbent articles such as diapers, sanitary napkins, and other articles for personal care and clinical use. Any of the wide variety of such polymers are suitable for use in the present invention. The predominant characteristic of these polymers is that they are capable of absorbing large quantities of liquids including water and aqueous solutions or suspensions, such as bodily exudates such as urine, menses and blood, and are further capable of retaining such liquids under moderate pressures. The polymers are at least substantially insoluble in water but capable of retaining at least about 10 times, preferably at least about 50 times, and most preferably from about 200 times to about 1000 times their weight of water or other aqueous-based fluid, and swelling in volume accordingly.

Various types of polymers function as superabsorbent polymers. Notable among these are polymers of acrylic or vinyl monomers that are slightly crosslinked with a polyfunctional reagent. Examples are polyacrylic acid, polyacrylamide, polyvinyl alcohol, polyvinyl pyrrolidone, guar gum, polyethylene oxide, sulfonated polystyrene, polysulfoethyl acrylate, poly(2-hydroxyethyl acrylate), starch modified polyacrylic acids and hydrolyzed polyacrylonitrile, plus alkali metal salts of the acids. Superabsorbent polymers of polyacrylic acid and polyacrylamide are preferred.

The preparation methods of superabsorbent polymers are many and varied. Acrylic acid and starch, for example, can be polymerized in an aqueous medium using a polyfunctional monomer such as N,N-alkylene-bis-acrylamide as a crosslinking agent, as described in U.S. Pat. No. 4,076,663 (Masuda et al., Sanyo Chemical Industries, Inc., issued Feb. 28, 1978). Alternatively, acrylic acid can be polymerized first, followed by crosslinking with an agent such as epichlorohydrin, as described in U.S. Pat. No. 4,340,706 (Obayashi et al., Seitetsu Kagaku Co., Ltd., issued Jul. 20, 1982). Further examples are found in U.S. Pat. Nos. 4,654,039 (Brandt et al., The Proctor & Gamble Company, issued Mar. 31, 1987), 3,669,103 (Harper et al., The Dow Chemical Company, issued Jun. 13, 1972), 3,670,731 (Harmon, Johnson & Johnson, issued Jun. 20, 1972), and 5,338,766 (Phan et al., The Proctor & Gamble Company, issued Aug. 16, 1994), and European Patent Application Nos. 644,207 (Nalco Chemical Company, published Mar. 22, 1995) and 547,474 (Hoechst Celanese Corporation, published Jun. 23, 1993). Each of these patents is incorporated herein by reference for all legal purposes that may be served thereby.

A variety of superabsorbent polymers suitable for use in the present invention are commercially available. Examples are SANWET®, a starch-modified superabsorbent polymer available from Hoechst Celanese Corporation, Charlotte, N.C., USA; DRYTECH®520, a superabsorbent polymer derived from propenoic acid, available from The Dow Chemical Company, Midland, Mich., USA; AQUAKEEP, available from Seitetsu Kagaku Co., Ltd., Hyogo, Japan; ARASORB, available from Arakawa Chemical (USA) Inc., Chicago, Ill., USA; ARIDALL 1125, available from Chemdall Corporation; and FAVOR, available from Stockhausen, Inc., Greensboro, N.C., USA.

Like the microfibrillar collagen, superabsorbent polymer can be used in any physical form which will permit high surface area contact with and absorption of the seeping blood, and which will permit an intimate mixture with the microfibrillar collagen. Effective forms of the mixture can include mixtures of particles where each component is in particle form; structures where one component is in particle form and the other a fabric, web or foam with interstices in which the particles are retained; and structures formed by interweaving fibers or webs of the two components.

For the superabsorbent polymer, the most common forms are foams and particles. Particles are particularly convenient for their ease of mixing with particles of the microfibrillar collagen in any desired proportion. When the superabsorbent polymer is in particle form, the particle size can vary widely and is not critical to this invention. For the most practical applications, the particles will have sizes lying substantially entirely within the size range of about 1 micron to about 1000 microns in diameter. A preferred size range is about 20 microns to about 500 microns in diameter, while a particularly preferred size range is about 100 microns to about 200 microns in diameter.

Other physical properties of the superabsorbent polymer can likewise vary. In general, however, for the most practical applications, the polymer will have a a surface area to mass ratio of at least about 0.2 m$^2$/g, and preferably at least about 3 m$^2$/g.

The relative amounts of microfibrillar collagen and superabsorbent polymer may vary widely while still producing an effective dressing serving the purposes of the invention. While no particular range is critical to the invention, in practical implementations of the invention the particle mixture will generally contain at least about 3% by weight of each of these two components. In preferred embodiments of the invention, the weight ratio of microfibrillar collagen to superabsorbent polymer is within the range of about 0.3:1 to about 30:1, more preferably about 1:1 to about 20:1, and most preferably about 3:1 to about 10:1. In one currently preferred dressing embodying this invention, the weight ratio is about 7:1.

The mixture of microfibrillar collagen and superabsorbent polymer is enclosed in an enclosure whose purpose is to contain the mixture and to allow rapid permeation of blood through the enclosure wall to the mixture. The enclosure is thus preferably hydrophilic, and also preferably flexible to permit full contact with the open wound and surrounding area. Any materials meeting this description will be acceptable. Examples are cloth fabric such as cotton or polyester. The enclosure is preferably expandable by a factor of from about 2 to about 100, and most preferably by a factor of from about 3 to about 30.

The dressing can assume any shape or size, depending on how it is to be used. While variations are possible, the enclosure (or liner sleeve, for dressings that contain additional external layers) will in general be substantially planar, i.e., with a length and width considerably exceeding its thickness. In most cases, the length and width will each exceed the thickness by a factor of at least about 10. The dressing itself will also preferably be flexible to be able to follow the contour of the body surface and provide full contact with the wound and surrounding area.

Further preferred dressing are those in which the enclosure portion is expandable to accommodate the expansion of the superabsorbent polymer upon absorption of fluid. Expandability is readily achieved by accordion folds along the perimeter of the enclosure, or other similar means which will be readily apparent to those knowledgeable in bandage construction.

For dressings in which the microfibrillar collagen and superabsorbent polymer mixture contains particular material, it is preferable to stabilize the particles against shifting inside the dressing, particularly during storage and transport. Stabilization is the most important when both components are in particle form. Stabilization can be achieved by mechanical means such as partitions, baffles, cells, or webs, all preferably of hydrophilic, porous and otherwise inert material. A presently preferred construction utilizes one or more partitions parallel to one or more of the edges of the enclosure and dividing the enclosure interior into compartments, lengthwise, widthwise or both. The partitions are impermeable to the microfibrillar collagen and superabsorbent polymer particles, yet permeable to the blood or other fluid. The partitions can also be expandable in construction, in the same manner as the perimeter walls of the enclosure.

Further features of the dressing whose inclusion is preferred for practical applications of the dressing are a porous topsheet on the side intended to face the wound, and a non-porous backsheet on the side away from the wound. The topsheet is preferably an adhesion-resistant material, although sufficiently permeable to allow rapid penetration by blood. One example of a useful material for this purpose is porous polypropylene fabric. The backsheet is primarily for purposes of protecting the dressing and the wound from the atmosphere and external contact. Any material with sufficient structural strength to serve this purpose and to withstand stretching forces typically encountered when the dressing is applied can be used. Nonporous polypropylene or a fluorinated polyurethane such as POLYFOX, which is available from Aerojet General Corporation, Sacramento, Calif., are examples.

While the quantities of materials and their dimensions can vary considerably, specific examples will be illustrative. According to one example, the enclosure or liner sleeve is rectangular in shape, with dimensions of 15 cm in length, 15 cm in width and 0.25 cm in thickness when dry. The four side edges of the liner sleeve are formed in an accordion-type manner, permitting expansion from a thickness of 0.25 cm to about 3.0 cm. The enclosure contains four parallel internal partitions, formed either by stitching or by walls, the latter being accordion-like in configuration and expandable in the same manner as the edge walls. The fronting or topsheet is 2 mils thick, and the backing or backsheet is 5 mils thick. The particle mixture contains 5 cm$^3$ of polyacrylic acid and 30 cm$^3$ of microfibrillar collagen, both at a particle size of about 100 microns in diameter.

According to a second example, the length of the linear sleeve is 20 cm, the width 14 cm, and the thickness when unexpanded is 0.3 cm, expandable to 3.0 cm. The collapsed volume of the sleeve interior is 84 cm$^3$ and the expanded volume 840 cm$^3$. Expandable partitions are included similar to those of the first example, the topsheet is 2 mils in thickness, and the backsheet is 2–5 mils in thickness. The particle mixture contains 4.2 cm$^3$ of polyacrylic acid and 30.0 cm$^3$ of collagen, at particle sizes within the range of 100–200 microns in diameter.

The dressing will be designed for use on various parts of the body, with appropriate securing devices and materials. For wounds on extremities, the dressing can be equipped with fastenings that will secure the dressing by encircling the extremity. Buckles, straps, rings and hook-and-loop fasteners (VELCRO®) are examples. For wounds on areas such as the torso or head, the dressing can be equipped with adhesive surrounding the perimeter of the active area of the dressing, or any other such means to achieve securement to a contoured surface.

Figure 1:
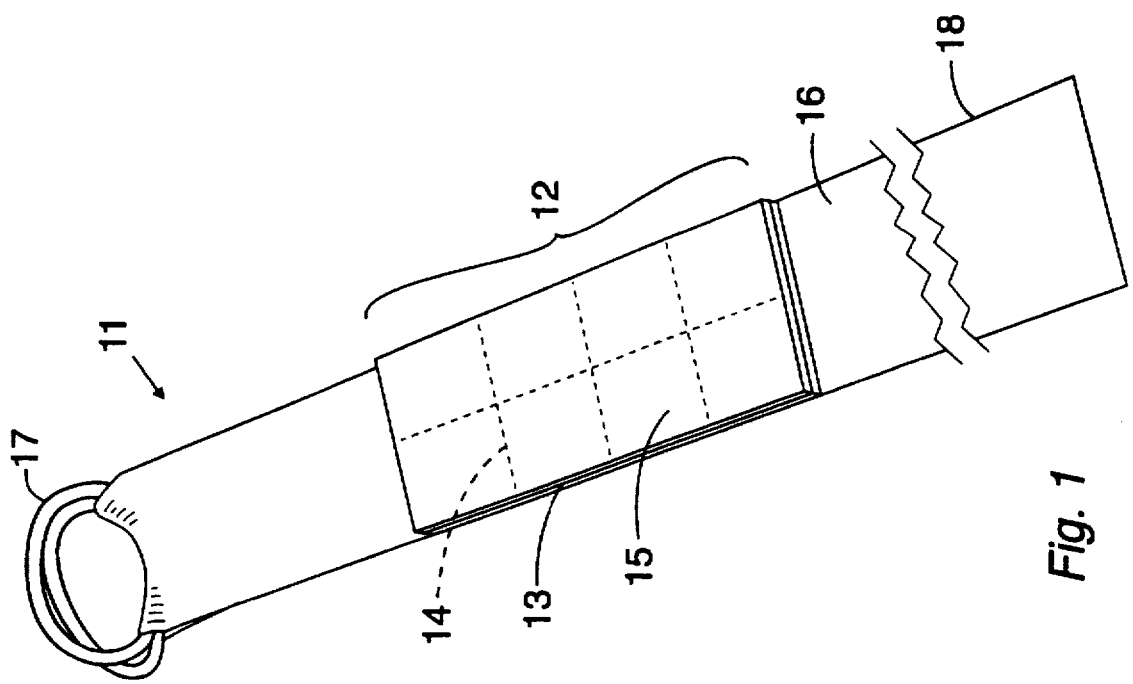
FIG. 1 is a perspective view of one example of a field dressing in accordance with this invention.

The drawings illustrate one particular embodiment of the invention. FIGS. 1 and 2 depict a field dressing or bandage 11 in the same perspective view with the active region 12 (the region designed to cover the wound itself and containing the microfibrillar collagen and superabsorbent polymer) both dry (FIG. 1) and swollen with blood (FIG. 2). The dressing in both figures is shown with the wound-facing side upwards (and therefore visible). The active region is rectangular and substantially flat, with the side edges 13 around all four sides having been formed into folds and therefore expandable from a folded configuration (FIG. 1) to an expanded configuration (FIG. 2). Dashed lines 14 in both FIGS. 1 and 2 indicate the location of partitions in the active region, dividing its interior into compartments. Each dashed line represents a folded piece of material similar to the folded outside edges 13 of the active region. The active region itself 12 is enclosed in a cloth enclosure, formed of the expandable side edges 13 and flat sheets at the top and bottom (not visible in FIGS. 1 and 2). The upper surface or top of the enclosure is covered with a porous topsheet 15 which will contact the wound surface, and a non-porous backsheet 16 which serves as the external (exposed) surface of the dressing once the dressing has been applied to the wound. The backsheet 16 extends lengthwise beyond the active region 12 of the bandage to serve as a means of securing the bandage to the wound region. In this particular embodiment, the fastening members consist of a pair of polypropylene rings 17 affixed to one end of the backsheet. The opposite end 18 of the backsheet will be passed through and back between the rings or otherwise secured to them.

Figure 3:
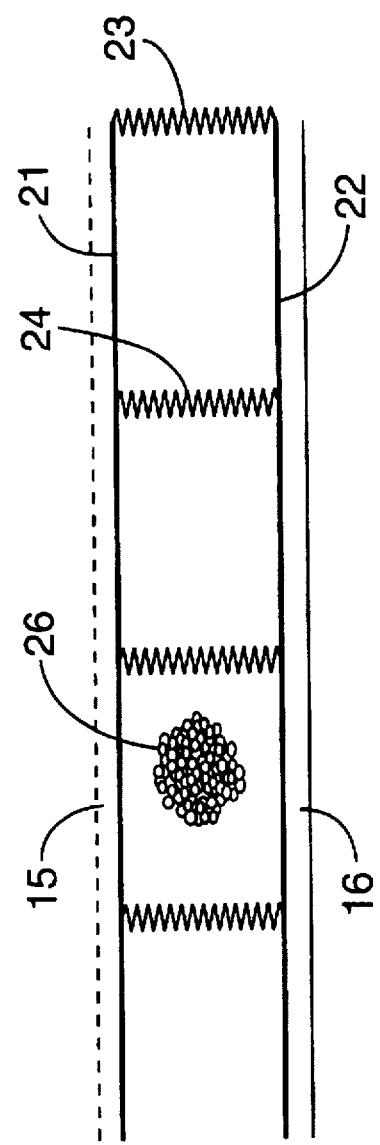
FIG. 3 is a longitudinal cross section of the active region of the dressing.

FIG. 3 is a cross section of the active region 12 of the dressing. The upper and lower flat sheets 21, 22 of the cloth enclosure are shown together with one expandable edge 23 of accordion-folded cloth. Internal partitions 24 are also shown, similarly made of accordion-folded cloth. The core 25 of the active region is filled with the particle mixture 26 of microfibrillar collagen and superabsorbent polymer particles. The porous topsheet 15 is laminated to one of the broad flat surfaces of the cloth enclosure, and the non-porous backsheet 16 is laminated to the other.

The foregoing is offered primarily for purposes of illustration. It will be readily apparent to those skilled in the art that the materials, proportions, dimensions, and other parameters of the system described herein may be further modified or substituted in various ways without departing from the spirit and scope of the invention.

We claim:

1. A dressing for an open wound, comprising a mixture of microfibrillar collagen and superabsorbent polymer, contained in an enclosure of flexible and blood-permeable material.

2. The dressing of claim 1 in which said enclosure is expandable to a degree necessary to accommodate volumetric expansion of said superabsorbent polymer upon absorption of blood thereby.

3. The dressing of claim 1 in which said enclosure is expandable by a factor of from about 2 to about 100.

4. The dressing of claim 1 in which said enclosure is expandable by a factor of from about 3 to about 30.

5. The dressing of claim 1 in which said enclosure contains means for stabilizing said mixture against shifting within said enclosure.

6. The dressing of claim 5 in which said means for stabilizing are comprised of at least one partition dividing said enclosure into compartments, and both said enclosure and said at least one partition are expandable to accommodate volumetric expansion of said superabsorbent polymer upon absorption of blood thereby.

7. The dressing of claim 1 in which said enclosure is substantially planar with length, width and thickness, said thickness being expandable upon expansion of said superabsorbent polymer, and said length and width each exceeding said thickness when in an unexpanded condition by a factor of at least about 10.

8. The dressing of claim 1 in which at least one of said microfibrillar collagen and said superabsorbent polymer is in the form of particles of about 1 micron to about 1000 microns in diameter.

9. The dressing of claim 1 in which said microfibrillar collagen and said superabsorbent polymer are each in particle form, each falling substantially entirely within the range of about 1 micron to about 1000 microns in diameter.

10. The dressing of claim 1 in which said microfibrillar collagen and said superabsorbent polymer are each in particle form, each falling substantially entirely within the range of about 20 microns to about 500 microns in diameter.

11. The dressing of claim 1 in which said microfibrillar collagen and said superabsorbent polymer are each in particle form, each falling substantially entirely within the range of about 100 microns to about 200 microns in diameter.

12. The dressing of claim 1 in which said microfibrillar collagen and said superabsorbent polymer each constitute at least about 3% by weight of said mixture.

13. The dressing of claim 1 in which said mixture has a microfibrillar collagen to superabsorbent polymer weight ratio ranging from about 0.3:1 to about 30:1.

14. The dressing of claim 1 in which said mixture has a microfibrillar collagen to superabsorbent polymer weight ratio ranging from about 1:1 to about 20:1.

15. The dressing of claim 1 in which said mixture has a microfibrillar collagen to superabsorbent polymer weight ratio ranging from about 3:1 to about 10:1.

16. The dressing of claim 1 in which said superabsorbent polymer is a member selected from the group consisting of crosslinked polyacrylic acid, crosslinked polyacrylamide, crosslinked polyvinyl alcohol, crosslinked polyvinyl pyrrolidone, guar gum, and crosslinked polyethylene oxide.

17. The dressing of claim 1 in which said superabsorbent polymer is a member selected from the group consisting of polyacrylic acid and polyacrylamide.

18. The dressing of claim 1 in which said superabsorbent polymer is a polymer having a water absorbency of at least about 10 grams per gram of polymer, and a surface area to mass ratio of at least about 0.2 $m^2/g$.

19. The dressing of claim 1 in which said superabsorbent polymer is a polymer having a water absorbency of at least about 50 grams per gram of polymer, and a surface area to mass ratio of at least about 3 $m^2/g$.

20. The dressing of claim 1 in which said microfibrillar collagen is derived from porcine tissue.

21. The dressing of claim 1 in which said microfibrillar collagen is derived from bone tissue.

22. The dressing of claim 1 in which said enclosure is substantially planar, said dressing further comprising a layer of porous material on a first substantially planar side of said enclosure, and a layer of substantially fluid impermeable material on a second substantially planar side of said enclosure opposing that of said layer of porous material.

23. The dressing of claim 22 in which said layer of porous material is a porous hydrophobic film.

24. The dressing of claim 1 further comprising means for securing said dressing to an open wound.

* * * * *